United States Patent [19]

Schaeffer

[11] Patent Number: 5,468,504
[45] Date of Patent: Nov. 21, 1995

[54] EFFERVESCENT PHARMACEUTICAL COMPOSITIONS

[75] Inventor: Alain E. E. Schaeffer, Evreux, France

[73] Assignee: Laboratoires Glaxo S.A., Paris, France

[21] Appl. No.: 396,533

[22] Filed: Feb. 28, 1995

Related U.S. Application Data

[63] Continuation of Ser. No. 75,527, Jun. 17, 1993, abandoned.

[30] Foreign Application Priority Data

Dec. 21, 1990 [GB] United Kingdom ................... 9027827

[51] Int. Cl.$^6$ ..................................................... A61K 9/46
[52] U.S. Cl. ........................... 424/466; 424/489; 424/501; 514/960
[58] Field of Search ..................................... 424/465, 466, 424/489, 501; 514/960

[56] References Cited

FOREIGN PATENT DOCUMENTS

| | | |
|---|---|---|
| 0203768 | 12/1986 | European Pat. Off. . |
| 0233853 | 8/1987 | European Pat. Off. . |
| 0396335 | 11/1990 | European Pat. Off. . |
| 2162522 | 2/1986 | United Kingdom . |

OTHER PUBLICATIONS

The Bantam Medical Dictionary (1981) pp. 196, 320.
Lieberman, Ed., "Pharmaceutical Dosage Forms", vol. 1—Tablets, 1980, 225–232.

*Primary Examiner*—Jyothsna Venkat
*Attorney, Agent, or Firm*—Bacon & Thomas

[57] ABSTRACT

The invention relates to effervescent pharmaceutical compositions for oral use comprising an effervescent couple consisting essentially of a base component and an acid component, which components react in the presence of water to generate a gas, and a compound which acts as a $5HT_1$-like receptor agonist or a physiologically acceptable salt or solvate thereof as active ingredient.

Methods for the manufacture of such compositions and for their use in the treatment of cephalic pain are also described.

8 Claims, No Drawings

EFFERVESCENT PHARMACEUTICAL COMPOSITIONS

This application is a Continuation of application Ser. No. 08/075,527, filed Jun. 17, 1993, now abandoned.

The present invention relates to a pharmaceutical composition containing as active ingredient a compound having selective agonist activity at $5HT_1$-like receptors, in particular a composition for oral administration.

5-$HT_1$-like receptors are located, for example, in the dog saphenous vein and the $5HT_1$-like receptor agonists with which the present invention is concerned contract the dog saphenous vein. Such compounds may therefore be identified by their contractile effect on the dog isolated saphenous vein strip as described, for example, by Apperley et. al., Br. J. Pharmacol, 68, 215–224, 1980). Compounds which are selective $5HT_1$-like receptor agonists have also been found to selectively constrict the carotid arterial bed of the anaesthetised dog.

A variety of compounds which selectively constrict the dog isolated saphenous vein strip and which constrict the carotid arterial bed of the anaesthetised dog have been described in the art. These include indole derivatives such as those disclosed inter alia in published French Patent Specifications Nos. 8115513, 8115514, 8115515, 8309429, 8418618, 8511790, 8518416, 8517858, 8700107, 8700108, 8708193 and published European Patent Specifications Nos. 147107, 237678, 242939, 244085, 225726, 254433, 303506, 303507, 354777 and 382570. The compounds disclosed in the specifications (hereinafter described as compounds A) are useful in the treatment of migraine and cluster headache.

The present invention provides an effervescent pharmaceutical composition for oral use comprising a compound which acts as a $5HT_1$-like receptor agonist, or a physiologically acceptable salt or solvate thereof, as active ingredient.

In a preferred embodiment of the invention we provide an effervescent pharmaceutical composition for oral use comprising one or more of compounds A or pharmaceutically acceptable salts or solvates thereof, as active ingredient.

Compositions according to the invention are preferably in a form adapted for use in medicine, in particular human medicine.

Oral administration constitutes a preferred route for administration of compounds A, and effervescent compositions provide a useful and advantageous type of formulation for oral use. Prior to being taken by the patient, an effervescent composition is dissolved and/or dispersed in, for example, an aqueous medium, such as drinking water. Desirably, dissolution and/or dispersion takes place rapidly with effervescence to give an agreeable presentation of the drug, particularly for patients who prefer not to take tablets or who have difficulty swallowing them. In addition, the solution or dispersion of the effervescent composition affords a liquid preparation containing a fixed dose of the drug, without any need for the patient to measure a prescribed volume. Anhydrous effervescent compositions according to the invention have been found to have excellent stability and formulation characteristics and to rapidly dissolve and/or disperse in water to provide an acceptable administration form of the drug.

A particularly preferred compound for use in the compositions of the present invention is 3-[2-(dimethylamino)ethyl]-N-methyl-1H-indole-5-methanesulphonamide.

3-[2-(dimethylamino)ethyl]-N-methyl-1H-indole-5-methanesulphonamide, which may be represented by the formula (I)

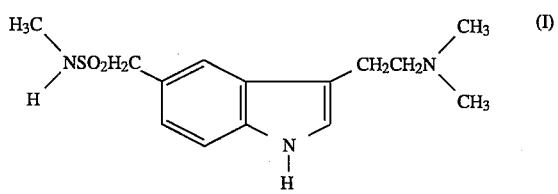

and physiologically acceptable salts and solvates thereof are disclosed in French Patent Specification No. 8511790. The compound of formula (I) exhibits selective vasoconstrictor activity and is useful in the treatment of migraine. French Patent Specification No. 8511790 contains reference to formulations for oral administration which may take the form of for example tablets, capsules, granules, powders, solutions, syrups, suspensions or tablets or lozenges for buccal administration.

There is thus provided in a particularly preferred aspect of the present invention an effervescent pharmaceutical composition for oral use comprising 3-[2 -(dimethylamino)ethyl]-N-methyl-1H-indole-5-methanesulphonamide, or a physiologically acceptable salt or solvate thereof, as active ingredient.

We have found that 3-[2-(dimethylamino)ethyl]-N-methyl-1H-indole-5-methanesulphonamide or a physiologically acceptable salt or solvate thereof is surprisingly advantageous when administered in the form of an effervescent composition.

It is highly desirable in the treatment of acute conditions such as migraine that pharmaceutical compositions have good bioavailability and a rapid onset of action. The effervescent formulations of the present invention have been determined to have excellent pharmacokinetic parameters. When compared to conventional tablet formulations, the effervescent tablets result in the drug being more rapidly absorbed into the plasma and may exhibit an enhanced onset of action.

Accordingly, a further aspect of the invention provides a method for the treatment of a mammal, including man, suffering from or susceptible to cephalic pain which comprises oral administration of an effervescent pharmaceutical composition comprising a compound which acts as a $5HT_1$-like receptor agonist, preferably 3-[2-(dimethylamino)ethyl]-N-methyl-1H-indole-5-methanesulphonamide or a physiologically acceptable salt or solvate thereof.

Conditions associated with cephalic pain include cluster headache, chronic paroxysmal hemicrania, headache associated with vascular disorders, headache associated with substances or their withdrawal (for example drug withdrawal), tension headache and in particular migraine. It will be appreciated that reference to treatment is intended to include prophylaxis as well as the alleviation of established symptoms.

It is preferred that 3-[2-(dimethylamino)ethyl]-N-methyl-1H-indole-5-methanesulphonamide should be employed in the compositions according to the invention in the form of a physiologically acceptable salt. Such salts include salts of inorganic or organic acids such as hydrochloride, hydrobromide, sulphate, nitrate, phosphate, formate, mesylate, citrate, benzoate, fumarate, maleate and succinate salts. Most preferably, 3-[2-(dimethylamino)ethyl]-N-methyl-1H-indole-5-methanesulphonamide will be employed in the compositions according to the invention in the form of its succinate (1:1) salt.

Effervescent formulations contain an effervescent couple consisting essentially of a base component and an acid component, which components react in the presence of water to generate a gas. In the compositions of the present invention, the base component may comprise, for example, an alkali metal or alkaline earth metal carbonate or bicarbonate, such as sodium bicarbonate, potassium bicarbonate, magnesium carbonate or calcium carbonate. The acid component may comprise, for example, an aliphatic carboxylic acid or a salt thereof, such as citric acid and salts thereof.

Preferably the base component in compositions according to the invention will comprise sodium bicarbonate.

Preferably the acid component in compositions according to the invention will comprise monosodium citrate.

It will be appreciated that the amount of compounds which act as $5HT_1$-like receptor agonists employed in the effervescent compositions of the invention will depend on the particular compounds used. Furthermore, the precise therapeutic dose employed will depend on the age and condition of the patient and the nature of the condition: to be treated and will be at the ultimate discretion of the attendant physician. In general, however, the amount of a compound having $5HT_1$-like activity will be in the range of 0.5 mg to 250 mg. The compositions may be administered for example 1 to 4 times per day, preferably once or twice.

The amount of 3-[2-(dimethylamino)ethyl]-N-methyl-1H-indole-5-methanesulphonamide, preferably in the form of a physiologically acceptable salt, employed in the effervescent compositions of the invention will preferably be in the range of 1 mg to 200 mg, most preferably 20 mg to 150 mg, for example about 100 mg, expressed as the weight of free base. The content of active ingredient of the effervescent composition (in the form of either free base or a physiologically acceptable salt) may be, for example, in the range of 1 to 20% on a weight-to-weight (w/w) basis.

The base and acid components may each independently constitute, for example 25% to 55% (w/w), more preferably 35% to 45% (w/w) of the effervescent composition. The ratio of acid component to base component may conveniently be within the range of 1:2 to 2:1, preferably 1:1.

Many drug substances have an inherently bitter taste. The taste of oral compositions containing compounds which act as $5HT_1$-like receptor agonists may be improved by the use of flavouring and/or sweetening agents. Suitable flavouring agents may be for example lemon, orange, grapefruit or mint flavouring. Suitable sweetening agents for use in the compositions of the invention include sucrose, sodium saccharin, cyclamic acid and alkali or alkali earth metal salts thereof, mannitol, nutrasweet R, acesulfame potassium, thaumatin or aspartame. One or more than one such flavouring and/or sweetening agents may be used.

Preferably effervescent compositions according to the invention will contain aspartame as sweetening agent.

A preferred effervescent composition according to the invention comprises 3-[ 2-(dimethylamino)ethyl]-N-methyl-1H-indole-5-methanesulphonamide succinate (1:1), monosodium citrate and sodium bicarbonate, together with aspartame as sweetening agent. More particularly, these four ingredients may be presented in amounts of 1% to 20% (w/w), 25% to 55% (w/w), 25% to 55% (w/w) and 1% to 4% (w/w) respectively.

The effervescent compositions of the invention may be formulated using additional physiologically acceptable carriers or excipients as appropriate. Such additional carriers or excipients are preferably water soluble or substantially water soluble, and may be for example binding agents such as polyvinylpyrrolidone and/or lubricants such as sodium benzoate or polyalkylene glycols. One or more dyes may also be included.

The compositions may take the form of, for example, tablets, granules or powders, granules or powders conveniently being presented as a fixed dose in a sachet. Preferably the compositions will be in the form of tablets.

When the effervescent compositions are formulated as tablets, these preferably contain 1% to 3% (w/w) of a binding agent, e.g. polyvinylpyrrolidone, and 2% to 4% (w/w)of a lubricant, e.g. sodium benzoate. When the effervescent compositions am formulated as granules or powders, presented in sachets, these preferably contain 2% to 4% (w/w) of a binding agent, such as polyvinylpyrrolidone.

The effervescent compositions of the invention may be prepared according to conventional techniques well known in the art of pharmacy for the manufacture of tablets, granules and powders.

Thus, for the preparation of effervescent compositions according to the invention, a compound having $5HT_1$-like agonist activity or a physiologically acceptable salt or solvate thereof, the acid component and the base component may be blended with suitable excipients and, if desired, granulated. Optionally, one or more sweetening agents may be added either before or after granulation. If the manufacturing process includes granulation, this should precede the addition of any flavouring agent(s). Tablets may be prepared, for example, by compression of the powder blend or granulate, using a lubricant as an aid to tabletting.

It is important that the compositions according to the invention should be manufactured, packed and stored under conditions of low moisture. Thus, for example, tablets may be packed individually in sealed strips made of a water-impervious material such as aluminium foil, or presented in suitable multidose containers (made from e.g. polypropylene) incorporating a dessicant, e.g. silica gel. Powders or granules may for example be presented in sealed water-impervious sachets, conveniently containing a single fixed dose.

The following example illustrates an effervescent composition according to the invention in which the active ingredient is 3-[2-dimethylamino)ethyl]-N-methyl- 1H-indole-5-methanesulphonamide succinate salt (1:1). Other compounds which act as agonists at $5HT_1$-like receptors may be formulated in a similar manner.

EXAMPLE 1

| Effervescent Tablet | |
|---|---|
| Active ingredient* | 140.0 mg |
| Sodium bicarbonate | 656.4 mg |
| Monosodium citrate anhydrous | 659.5 mg |
| Aspartame | 40.0 mg |
| Polyvinylpyrrolidone | 32.0 mg |
| Sodium benzoate | 48.0 mg |
| Orange flavour IFF 29G44 | 16.0 mg |
| Lemon flavour IFF 29M194 | 8.0 mg |
| Absolute alcohol for granulation | |

*3-[2-dimethylamino)ethyl]-N-methyl-1H-indole-5-methanesulphonamide succinate salt (1:1), equivalent to 100 mg free base.

The active ingredient, anhydrous monosodium citrate, sodium bicarbonate and aspartame were mixed together and granulated by the addition of a solution of the polyvinylpyrrolidone in the alcohol. The granules obtained after mixing were dried and passed through a calibrator, and the resulting granules were then mixed with the sodium benzoate and flavourings. The granulated material was compressed into tablets using an alternative machine fitted with 20 mm punches.

A rotative machine fitted with 20 mm punches may also be used for tabletting.

I claim:

1. An effervescent pharmaceutical composition for oral use for migraine comprising 20 mg to 150 mg of a compound which is 3-[2-(dimethylamino)ethyl]-N-methyl-1H-indole-5-methanesulphonamide succinate (1:1) salt as the active ingredient and 25% to 55% (w/w) sodium bicarbonate as the base component and 25% to 55% (w/w) monosodium citrate as acid component, which components react in the presence of water to generate a gas.

2. A pharmaceutical composition as claimed in claim 1 which contains about 100 mg of active ingredient per unit dose (expressed as the weight of free base).

3. A pharmaceutical composition as claimed in claim 1 which further comprises one or more flavouring and/or sweetening agents.

4. A pharmaceutical composition as claimed in claim 1 which further comprises 1% to 4% (w/w) binding agent.

5. A pharmaceutical composition as claimed in claim 1 which further comprises 2% to 4% (w/w) lubricant.

6. A pharmaceutical composition as claimed in claim 1 in the unit dosage form of tablets.

7. A method for the treatment of a mammal, including man, suffering from or susceptible to migraine, which comprises orally administering an effective amount of an effervescent pharmaceutical composition of claim 1.

8. A method for the treatment of a mammal, including man, suffering from or susceptible to migraine, which comprises orally administering an effective amount of an effervescent pharmaceutical composition of claim 2.

* * * * *